(12) United States Patent
Martin et al.

(10) Patent No.: US 8,290,224 B2
(45) Date of Patent: Oct. 16, 2012

(54) METHOD AND DEVICE FOR IMAGING CYCLICALLY MOVING OBJECTS

(75) Inventors: Diana Martin, Herzogenaurach (DE); Sebastian Schmidt, Weisendorf (DE)

(73) Assignee: Siemens Aktiengesellschaft, Munich (DE)

( * ) Notice: Subject to any disclaimer, the term of this patent is extended or adjusted under 35 U.S.C. 154(b) by 1023 days.

(21) Appl. No.: 12/071,659

(22) Filed: Feb. 25, 2008

(65) Prior Publication Data

US 2008/0219510 A1 Sep. 11, 2008

(30) Foreign Application Priority Data

Feb. 26, 2007 (DE) .................. 10 2007 009 182

(51) Int. Cl.
*G06K 9/00* (2006.01)
(52) U.S. Cl. ........ 382/128; 382/129; 382/130; 382/131; 382/294; 600/410
(58) Field of Classification Search .......... 382/128–131, 382/294; 600/410
See application file for complete search history.

(56) References Cited

U.S. PATENT DOCUMENTS

| | | | | |
|---|---|---|---|---|
| 4,855,910 A * | 8/1989 | Bohning | .................. | 324/309 |
| 4,885,910 A * | 12/1989 | Resch | .................. | 60/562 |
| 5,672,877 A * | 9/1997 | Liebig et al. | .................. | 250/363.04 |
| 6,171,241 B1 * | 1/2001 | McVeigh et al. | .................. | 600/410 |
| 6,603,991 B1 * | 8/2003 | Karmalawy et al. | .................. | 600/411 |
| 6,798,199 B2 * | 9/2004 | Larson et al. | .................. | 324/309 |
| 7,043,063 B1 | 5/2006 | Noble et al. | | |
| 7,117,026 B2 * | 10/2006 | Shao et al. | .................. | 600/411 |
| 2003/0123718 A1 * | 7/2003 | Edic et al. | .................. | 382/131 |
| 2005/0238215 A1 | 10/2005 | Jolly et al. | | |
| 2006/0004275 A1 * | 1/2006 | Vija et al. | .................. | 600/407 |
| 2006/0025669 A1 * | 2/2006 | Ramamurthy et al. | .................. | 600/407 |
| 2006/0052685 A1 * | 3/2006 | Cho et al. | .................. | 600/407 |
| 2006/0235295 A1 * | 10/2006 | Boese et al. | .................. | 600/428 |
| 2006/0239524 A1 * | 10/2006 | Desh et al. | .................. | 382/128 |
| 2006/0258933 A1 * | 11/2006 | Ellis et al. | .................. | 600/407 |
| 2006/0266947 A1 | 11/2006 | Krieg et al. | | |
| 2007/0081703 A1 * | 4/2007 | Johnson | .................. | 382/128 |

(Continued)

FOREIGN PATENT DOCUMENTS

DE 10310127 9/2004

(Continued)

OTHER PUBLICATIONS

Fusion—effects., Calvini et al., IEEE, 0018-9499, 2006, pp. 189-197.*

(Continued)

*Primary Examiner* — Jayesh A Patel
(74) *Attorney, Agent, or Firm* — Harness, Dickey & Pierce, P.L.C.

(57) ABSTRACT

A method and a device are disclosed for imaging cyclically moving objects using a first and a second imaging method which differ at least with regard to the spatial resolution or the sensitivity. In at least one embodiment of the process, images of the object are continuously recorded by the first imaging method. Temporally different phases of a movement cycle of the object are extracted from the images recorded by the first imaging method. Images of the object are recorded by the second imaging method. The image data recorded in each case in a same, repeating phase of the of the movement cycle by the second imaging method are summed and temporally assigned to the different phases of the movement cycle.

10 Claims, 3 Drawing Sheets

U.S. PATENT DOCUMENTS

| | | | |
|---|---|---|---|
| 2007/0197907 A1* | 8/2007 | Bruder et al. | 600/425 |
| 2007/0272868 A1 | 11/2007 | Krieg et al. | |
| 2008/0095414 A1* | 4/2008 | Desh et al. | 382/128 |
| 2008/0226149 A1* | 9/2008 | Wischmann et al. | 382/131 |
| 2009/0326362 A1* | 12/2009 | Carlse et al. | 600/411 |

FOREIGN PATENT DOCUMENTS

| | | |
|---|---|---|
| DE | 102006015749 | 4/2006 |
| DE | 102005023907 | 12/2006 |
| WO | WO 0116886 | 3/2001 |
| WO | WO 2006083588 | 8/2006 |

OTHER PUBLICATIONS

Andrew C. Larson et al. "Preliminary Investigation of Respiratory Self-Gating for Free-Breathing Segmented Cine MRI", Magnetic Resonance in Medicine 53: 159-168 (2005); Others.

A. Seeger et al. "Myocardial Tagging", comparison at 1.5 Tesla and 3 Tesla in a volunteer study, ESMRMB 2006; Others.

* cited by examiner

METHOD AND DEVICE FOR IMAGING CYCLICALLY MOVING OBJECTS

PRIORITY STATEMENT

The present application hereby claims priority under 35 U.S.C. §119 on German patent application number DE 10 2007 009 182.8 filed Feb. 26, 2007, the entire contents of which is hereby incorporated herein by reference.

FIELD

Embodiments of the present invention generally relate to a method and/or a device for imaging cyclically moving objects using a first and a second imaging method which differ at least with regard to the spatial resolution or the sensitivity. The method and the device for imaging, in at least one embodiment, may be particularly suited for medical interventions.

BACKGROUND

So-called "hybrid modalities", such as, for example, PET/CT, SPECT/CT, MR/PET and MR/SPECT, have recently been becoming increasingly important in medical imaging. In this context, PET is positron emission tomography,
CT is computed tomography,
SPECT is single photon emission computed tomography,
MR is magnetic resonance tomography, and
NM is nuclear medical imaging.

Combining a modality with a high spatial resolution (preferably MR or CT) and a modality with high sensitivity (preferably nuclear medicine such as, for example, SPECT or PET, abbreviated as NM in the following) is advantageous in these combinations.

Movement unsharpness, which has a particularly strong effect on the heart, which beats cyclically during the examination and thus has considerable movement unsharpness, is a particular problem in the case of PET and SPECT, making it very difficult to assign the PET/SPECT signal to particular regions of the heart. This removes the advantage of the high spatial resolution of the combined modality. This problem is particularly unfavorable in the case of examining patients with heart diseases, who have an irregular or very high heart rate.

FIG. 1 clarifies the problem. Reference symbol 1 denotes a heart. Reference symbols 2 and 3 denote the heart wall during systole or diastole. The reference symbols V and V' in each case denotes a particular voxel of the heart wall during the systole or diastole. From FIG. 1, it is clear that the particular voxel undergoes a transition V'-V between diastole and systole during a cardiac cycle, leading to the described movement unsharpness.

The prior art discloses so-called gating techniques, which are based on ECG signals. For this purpose, ECG electrodes are applied to the patient. An algorithm identifies R waves in the ECG signal and uses these to determine the cardiac phases, the R wave being the first positive deflection in the QRS complex. Subsequently, use is made only of the measurement data which fall into a particular cardiac phase (for example, the diastole). Up until now, movement artifacts have been satisfactorily compensated by this method.

However, these methods still have a number of disadvantages. Applying ECG electrodes is an additional, time-consuming procedural step. In the case of MR, the electromagnetic fields interfere with the ECG electrodes, requiring the use of special ECG systems. Nevertheless, it is not always possible to receive a signal of adequate quality.

Due to the discarding of data, the measuring time is only partly used, and thus increases accordingly.

In the case of patients with previous cardiac disorders, the ECG signal is often pathologically changed, so that the algorithm for automatically detecting the R waves does not function.

DE 10 2005 023 907 A1 discloses a known method, which enables improvement with regard to spatial blurring when displaying PET data.

SUMMARY

In at least one embodiment of the present invention, a method and/or a device are provided for imaging objects undergoing periodic movement using a first and a second imaging method which differ at least with regard to the spatial resolution or the sensitivity, it being possible for the method and the device to compensate the movement unsharpness caused by the cyclic movements such as, for example, cardiac movements, without using ECG electrodes. Furthermore, the signal/noise ratio is to be improved.

At least one embodiment of the inventive method for imaging cyclically moving objects uses a first and a second imaging method, which differ at least with regard to the spatial resolution or the sensitivity.

Furthermore, at least one embodiment of the inventive method for imaging comprises:

continuously recording image data of the object by the first imaging method;

extracting temporally different phases of a movement cycle of the object from the image data recorded by the first imaging method;

recording images of the object by the second imaging method; and assigning the image data recorded by the second imaging method to the different phases of the movement cycle.

According to at least one embodiment of the invention, the method also has a step for summing (also referred to as "temporal integration" of) image data recorded in each case in a same, repeating phase of the movement cycle by the second imaging method.

In this context, the object can be a heart, in which the temporally different phases could be the diastole and the systole respectively. Here, a repeating movement cycle extends from the diastole to the systole, or vice versa.

The extracted, temporally different phases of a movement cycle of the object from the image data recorded by the first imaging method are preferably assigned to cyclically successive times. The image data of the object are recorded in list mode by the second imaging method and are stored in a table with a time stamp. The assignment of the image data recorded by the second imaging method to the different phases of the movement cycle is effected on the basis of matching the cyclically successive times and the time stamps.

The extraction of the different phases of the movement cycle of the object from the image data recorded by the first imaging method is preferably effected by a two-dimensional segmentation of the object, a three-dimensional segmentation of the object, a surface measurement or volumetry.

The method preferably has a step for superposed display of the image data recorded by the first imaging method and the image data recorded by the second imaging method.

The method preferably has a step for determining a movement vector of an object point of the object between two predetermined phases of the movement cycle on the basis of the image data recorded by the first imaging method, and a step for translating object points of the image data recorded by the second imaging method by means of the movement vector between the two predetermined phases.

The first imaging method is preferably a magnetic resonance tomography (MR) method. The use of computed tomography (CT) is also possible, but less preferred due to the radiation exposure associated with the time-resolved measurement.

The second imaging method is preferably a single photon emission computed tomography (SPECT) method or a positron emission tomography (PET) method.

A device is disclosed, in at least one embodiment, which carries out the method described above.

DETAILED DESCRIPTION OF THE EXAMPLE EMBODIMENTS

Figure 1:
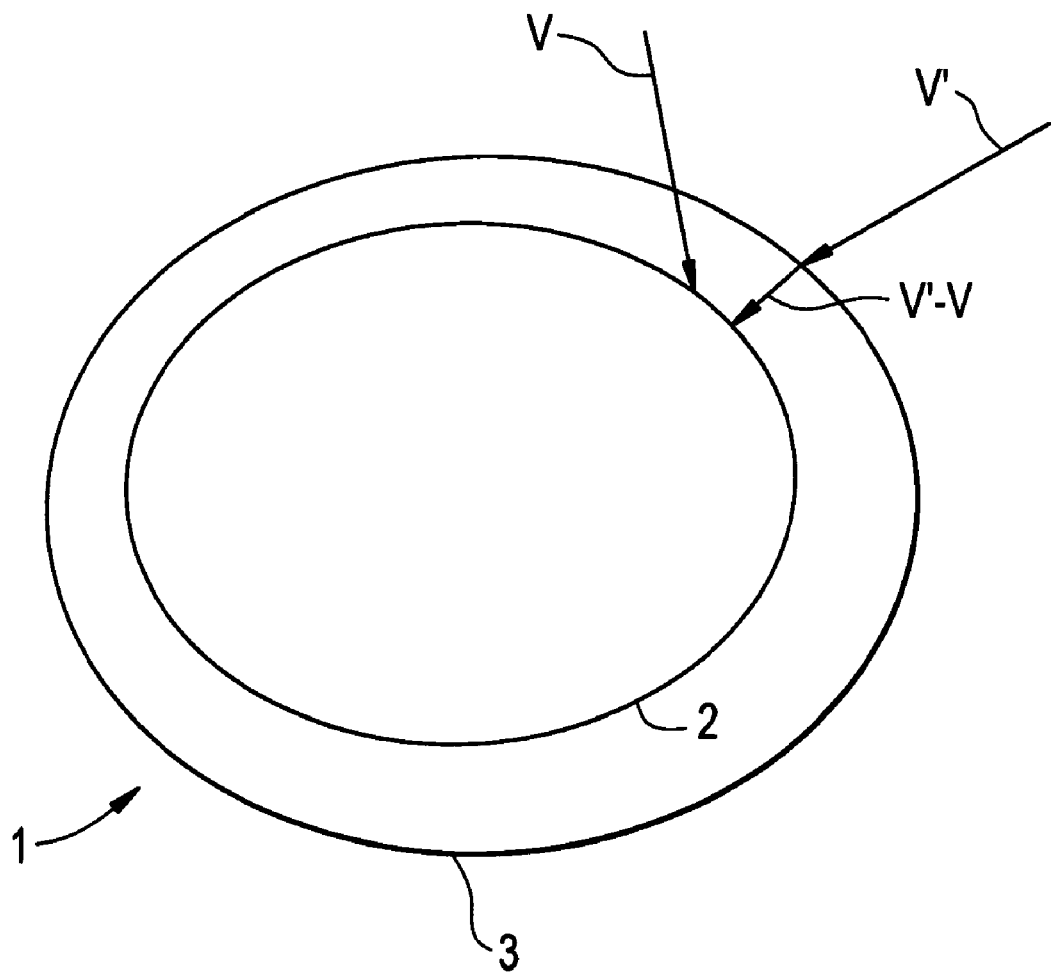
FIG. 1 shows a schematic diagram of a heart at two different phases of the cardiac cycle.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

An example embodiment of the invention is now described in more concrete terms.

Figure 2:
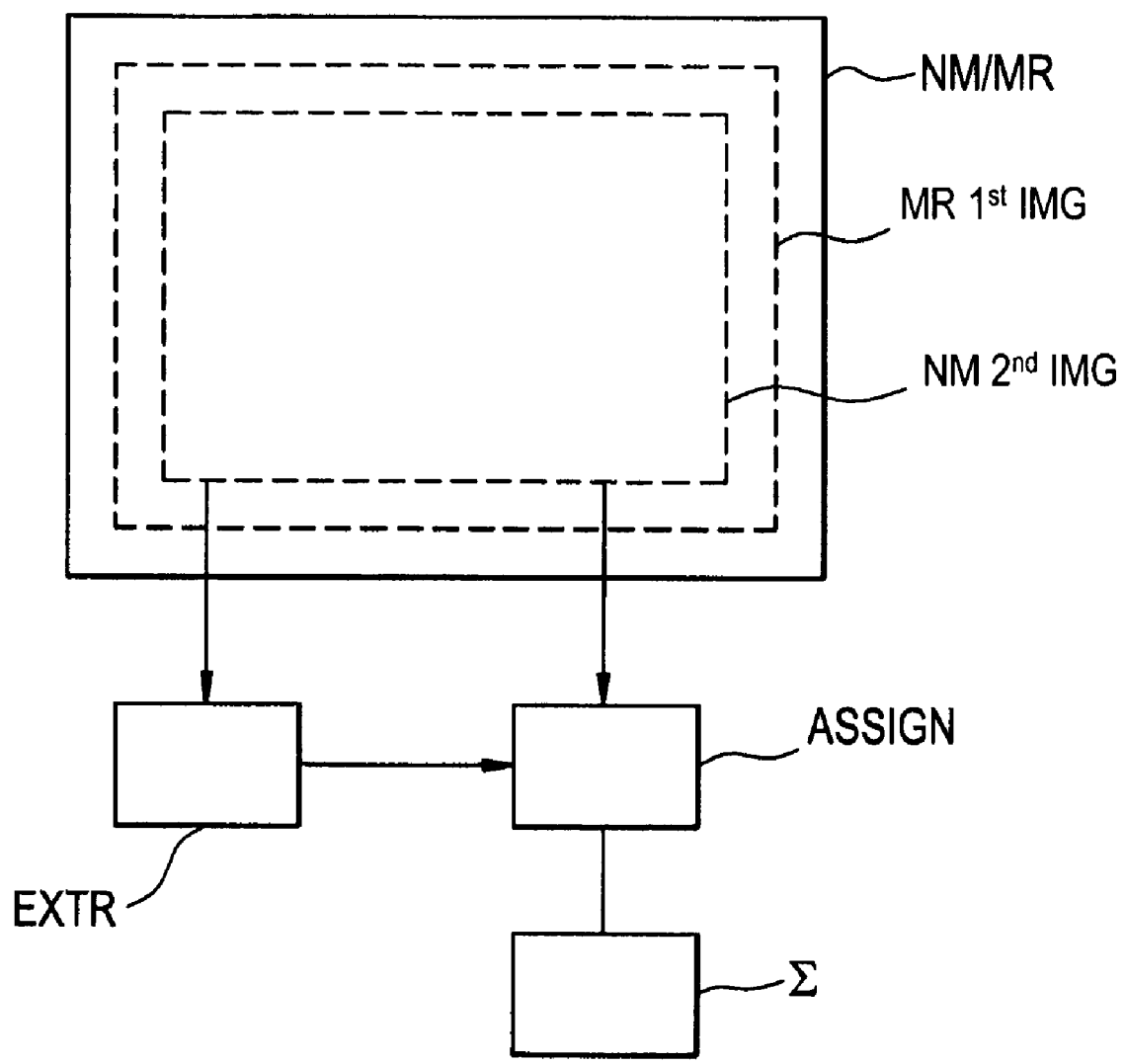
FIG. 2 shows a schematic diagram of an imaging device according to an example embodiment.

Referring now to FIG. 2, a schematic diagram of a combined MR/NM apparatus is illustrated, according to an example embodiment, that may include, for example, an MR/PET or an MR/SPECT, which allows simultaneous and isocentric measurement of MR and NM data.

Figure 3:
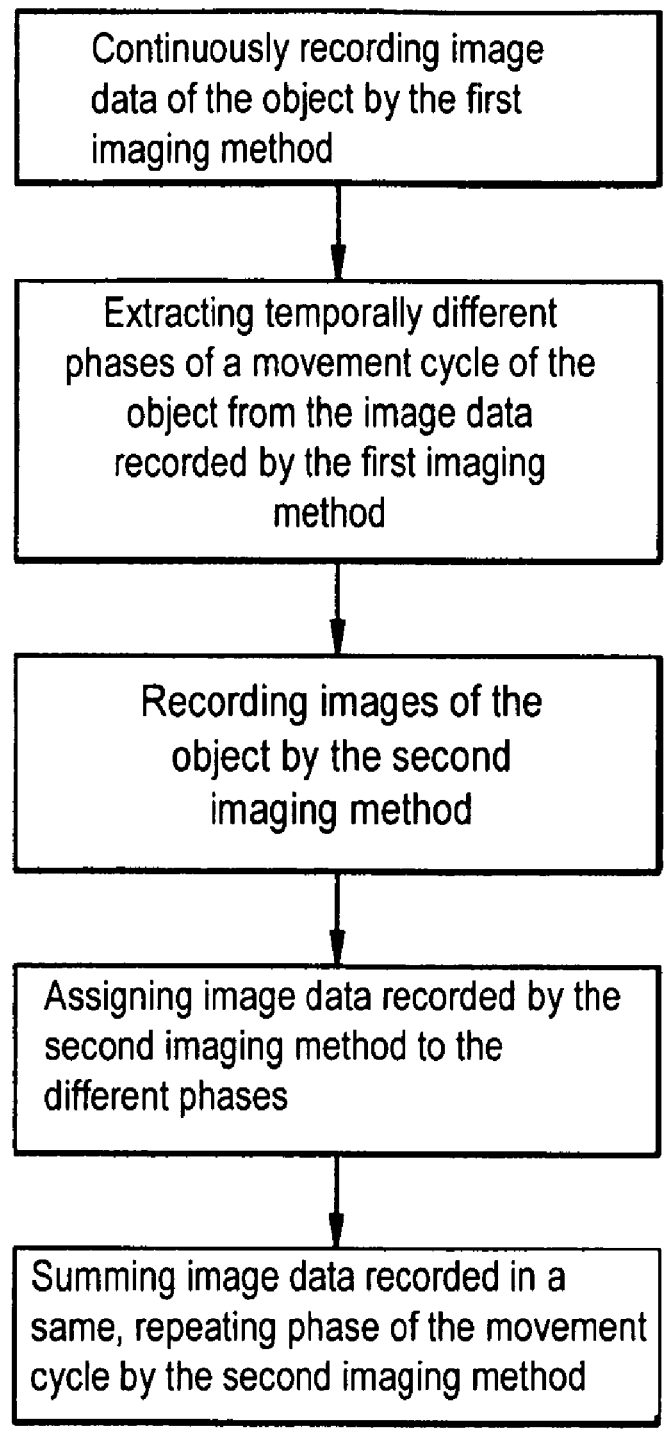
FIG. 3 shows a process flow diagram of an imaging method according to an example embodiment.

Referring now to FIG. 3, a method for imaging at least one cyclically moving object using a first and a second imaging method is shown according to an example embodiment. The first and second imaging methods may differ at least with regard to at least one of spatial resolution and sensitivity. A device for imaging may continuously record image data of the object by the first imaging method. The device may extract temporally different phases of a movement cycle of the object from the image data recorded by the first imaging method. The device may record an image data of the object by the second imaging method. The device may assign the image data recorded by the second imaging method to the extract temporally different phases of the movement cycle. The device may sum the image data recorded in a same, repeating phase.

The MR measurement, being the first imaging method, is carried out continuously simultaneously during the NM measurement, which is the second imaging method. In this case, sequences are used which enable the acquisition of the relevant volume with a high temporal resolution (for example, cine-true FISP). Such a method was not possible with the conventional PET and CT methods, because the radiation exposure would be too high for the patient. The acquisition can be carried out using time-resolved 2D or 3D techniques. The time of the acquisition is stored together with the MR data.

The NM measurement, being the second imaging method, is carried out in list mode in the described exemplary embodiment; in this case all individual measurement events are stored in a list together with a time stamp.

The cardiac phase is determined from the data of the MR measurement. As a result, the same cardiac phases, that is to say cyclically repeating cardiac phases, can be assigned to cyclically successive times. This can be achieved either via a 2D or 3D segmentation and surface measurement or volumetry, or else by application of "self-gating methods."

Alternatively, the cardiac phase is determined in k-space. For this purpose, a suitable method is disclosed in, for example, U.S. Pat. No. 6,798,199, the entire contents of which is hereby incorporated herein by reference.

A method for the segmentation of the heart chambers is described, inter alia, in PCT/US/06/02154 (the entire contents of which is hereby incorporated herein by reference), in which the term segmentation means the determination of local object features which enable a differentiation of the object from other objects and from the background, and which allow a determination as to whether an pixel belongs to an object.

A known self gating method is described in, for example, Magn Reson Med. 2005 January; 53(1): 159-68, the entire contents of which is hereby incorporated herein by reference.

In the described example embodiment the data of the NM measurement, preferably PET data, are assigned to the corresponding cardiac phases determined by the MR measurement using the time stamp and reconstructed separately for each cardiac phase, summation taking place over a plurality of cardiac cycles. In the simplest case, this generates a diastolic data set and a systolic data set. Additional intermediate phases can be reconstructed, if appropriate.

In the described example embodiment film is used for displaying in the most favorable case, the PET images and MR images being superposed. For this, measurements are taken over a plurality of cardiac cycles and subsequently summed over a plurality of data sets which are respectively to be assigned to the same time in the cardiac cycle.

In the segmented MR data sets, corresponding voxels from the heart wall during systole and diastole are determined by a method of non-rigid transformation. By way of example, this can be achieved by a method for non-rigid transformation, as disclosed by WO01/16886, for example, the entire contents of which is hereby incorporated herein by reference. The movement vector from diastole to systole is determined for each of these voxels and applied to the NM voxel. Thus, the NM data acquired during systole can be used completely for the reconstruction of an image of the heart during diastole without movement artifacts (or vice versa).

A method for correcting breathing movements, which is disclosed, for example, by DE 102 006 015 749 A1, the entire contents of which is hereby incorporated herein by reference, can be applied simultaneously.

In order to ease finding corresponding voxels in the MR data, it is possible to apply the method of "cardiac tagging", which is described, for example, in Seeger et al, ESMRMB 2006, the entire contents of which is hereby incorporated herein by reference.

The MR measurement uses methods which increase the jump in contrast between the heart wall and the surroundings (blood and the pericardial sac) in order to ease segmentation. Known methods of this type are, for example, dispensing of contrast agents, fat saturation or black blood techniques.

The invention is not restricted by the disclosed example embodiments; rather, modifications and equivalent embodiments are possible within the scope of the invention, which is defined by the claims.

In particular, the application of embodiments of the invention are not restricted to the cardiac cycle: rather, it can be used for any desired objects with cyclic movements. For example, embodiments of the invention can also be applied to the lung, which carries out a cyclic breathing movement.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for imaging at least one cyclically moving object using a first and a second imaging method differing at least with regard to at least one of spatial resolution and sensitivity, the method comprising:
   continuously recording image data of the object by a magnetic resonance tomography (MR) method;
   extracting temporally different phases of a movement cycle of the object from the image data recorded by the MR method;

simultaneously recording image data of the object by a single photon emission computed tomography (SPECT) method or a positron emission tomography (PET) method;

assigning the image data recorded by the SPECT or PET method to the extracted temporally different phases of the movement cycle;

summing the image data recorded by the SPECT or PET method, wherein the image data summed is, in each case, in a same, repeating phase of the movement cycle;

determining a movement vector of an object point of the object between two phases of the movement cycle on the basis of the image data recorded by the MR method; and translating object points of the image data recorded by the SPECT or PET method by use of the movement vector between the two phases, wherein the image data of the MR method are MR data, which are evaluated in k-space.

2. The method as claimed in claim 1, wherein the extracted, temporally different phases of the movement cycle of the object are assigned to cyclically successive times using the image data recorded by the MR method; and wherein the image data of the object are recorded in list mode by the SPECT or PET method and stored in a table with a time stamp, assignment of the image data recorded by the SPECT or PET method to the different phases of the movement cycle being effected on the basis of matching the cyclically successive times and the time stamps.

3. The method as claimed in claim 1, wherein the extraction of different phases of the movement cycle of the object from the image data recorded by the MR method is effected by at least one of a two-dimensional segmentation of the object, a three-dimensional segmentation of the object, a surface measurement and volumetry.

4. The method as claimed in claim 1, further comprising: superimposing display of the image data recorded by the MR method and the image data recorded by the SPECT or PET method.

5. The method as claimed in claim 1, wherein the object is a heart.

6. The method as claimed in claim 2, wherein the extraction of different phases of the movement cycle of the object from the image data recorded by the MR method is effected by at least one of a two-dimensional segmentation of the object, a three-dimensional segmentation of the object, a surface measurement and volumetry.

7. The method as claimed in claim 2, further comprising: superimposing display of the image data recorded by the MR method and the image data recorded by the SPECT or PET method.

8. A non-transitory computer readable medium including program segments for, when executed on a computer device, causing the computer device to implement the method of claim 1.

9. A device for imaging at least one cyclically moving object, comprising:

a first recording device to continuously record image data of the object by a magnetic resonance tomography (MR) method;

an extraction device to extract temporally different phases of a movement cycle of the object from the image data recorded by the magnetic resonance tomography (MR) method;

a second recording device to record image data of the object by a single photon computed tomography (SPECT) method or a positron emission tomography (PET) method, the second recording device differing from the first recording device with regard to at least one of spatial resolution and sensitivity;

an assignment device to assign the image data recorded by the SPECT or PET method to the different phases of the movement cycle;

a summing device to sum image data recorded by the second recording device, wherein the image data summed is, in each case, in a same, repeating phase of the movement cycle;

determining a movement vector of an object point of the object between two phases of the movement cycle on the basis of the image data recorded by the MR method; and translating object points of the image data recorded by the SPECT or PET method by use of the movement vector between the two phases, wherein the image data of the MR method are MR data, which are evaluated in k-space.

10. A device for imaging at least one cyclically moving object, comprising:

means for continuously recording image data of the object by a magnetic resonance (MR) tomography method;

means for extracting temporally different phases of a movement cycle of the object from the image data recorded by the magnetic resonance tomography (MR) method;

means for simultaneously recording image data of the object by a single photon computed tomography (SPECT) method or a positron emission tomography (PET) method;

means for assigning the image data recorded by the SPECT or PET method to the extracted temporally different phases of the movement cycle;

means for summing the image data recorded by the SPECT or PET method, wherein the image data summed is, in each case, in a same, repeating phase of the movement cycle;

means for determining a movement vector of an object point of the object between two phases of the movement cycle on the basis of the image data recorded by the MR method; and means for translating object points of the image data recorded by the SPECT or PET method by use of the movement vector between the two phases, wherein the image data of the MR method are MR data, which are evaluated in k-space.

* * * * *